:::

United States Patent
Durand et al.

(10) Patent No.: US 7,157,258 B2
(45) Date of Patent: Jan. 2, 2007

(54) PARTICLES CONTAINING COATED LIVING MICRO-ORGANISMS, AND METHOD FOR PRODUCING SAME

(75) Inventors: Henri Durand, Ramonville Saint-Agnes (FR); Jerome Panes, Toulouse Cedex (FR)

(73) Assignee: Lallemand S.A., Blagnac (FR)

( * ) Notice: Subject to any disclaimer, the term of this patent is extended or adjusted under 35 U.S.C. 154(b) by 185 days.

(21) Appl. No.: 10/221,646

(22) PCT Filed: Mar. 16, 2001

(86) PCT No.: PCT/FR01/00797

§ 371 (c)(1),
(2), (4) Date: Sep. 16, 2002

(87) PCT Pub. No.: WO01/68808

PCT Pub. Date: Sep. 20, 2001

(65) Prior Publication Data

US 2003/0109025 A1    Jun. 12, 2003

(30) Foreign Application Priority Data

Mar. 16, 2000 (FR) ................... 00 03409

(51) Int. Cl.
*C12N 11/02* (2006.01)
*C12N 1/20* (2006.01)
*C12N 1/15* (2006.01)
*A01N 63/00* (2006.01)
*A61K 9/28* (2006.01)

(52) U.S. Cl. .................. 435/177; 427/2.14; 424/93.4; 424/93.44; 435/252.1; 435/253.4

(58) Field of Classification Search ............... 424/93.4, 424/93.44; 435/252.1, 253.4, 177; 427/2.14
See application file for complete search history.

(56) References Cited

U.S. PATENT DOCUMENTS 4,888,171 A   12/1989   Okonogi et al.
5,507,871 A   4/1996    Morino et al.

FOREIGN PATENT DOCUMENTS

DE   37 38 599   5/1989
WO   92/12234    7/1992

*Primary Examiner*—Herbert J. Lilling
(74) *Attorney, Agent, or Firm*—Young & Thompson

(57) ABSTRACT

Particles containing dehydrated living micro-organisms are coated with a homogeneous layer of hydrophobic substance selected to reduce the risks of degradation of the micro-organisms by physico-chemical stresses such as heat, humidity, gastric acid, or compression. A method for producing such particles includes injecting a melting hydrophobic substance into the mass of the dehydrated micro-organisms placed in a chamber swept by an air stream at controlled temperature, where the base is rotating.

20 Claims, 1 Drawing Sheet

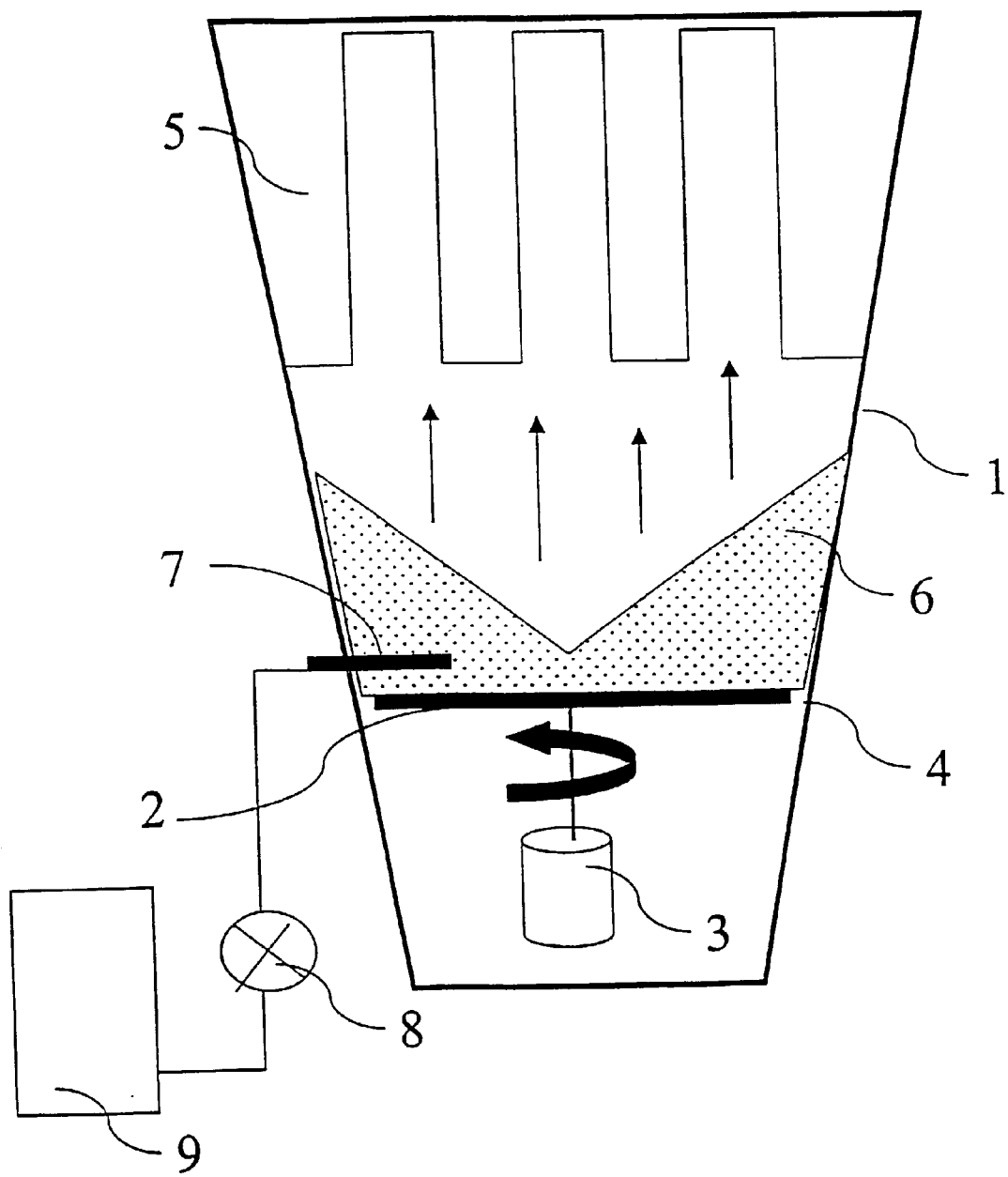

PARTICLES CONTAINING COATED LIVING MICRO-ORGANISMS, AND METHOD FOR PRODUCING SAME

The present invention relates to particles containing dehydrated living microorganisms, coated with a substance which makes it possible to increase the resistance of said microorganisms to physico-chemical stresses such as heat, humidity, acidity or compression. The present invention relates equally to a method of producing such particles and to the particles capable of being obtained by said method, and to their application in pharmaceutical, dietary or food compositions.

The use of dehydrated living microorganisms in pharmaceutical, dietary or food-processing applications, often means that during their manufacture, their storage or their use, these microorganisms are submitted to physico-chemical stresses such as for example conditions of raised pressure, temperature, humidity or acidity. This affects their capacity for resuming normal activity after rehydration, when their survival rate is not simply extremely reduced by the aggressiveness of such treatment.

Various solutions have been proposed which aim at covering the microorganisms with a protective substance.

For example the patent U.S. 99/06746 teaches the coating of bacteria with polymers, such as polyacrylamides, or copolymers associated with phospholipids. However, such polymers are not authorised in pharmaceutical or food products.

The patent FR 96 06215 describes the coating of bacteria with polymers or water-soluble polysaccharides, which excludes any stabilisation in an aqueous medium. In particular, for the preservation of products containing dehydrated microorganisms, it is imperative to guarantee a very low humidity level so that it is not possible for there to be any resumption of activity before it is used in the desired medium.

This is why other methods have been proposed using as a protective material substances which are edible and resistant to humidity.

According to the method described in the document DE 3738599, yeasts are encapsulated in fats, such as esters of fatty acids, the softening temperature of which is greater than 29° C. In this way the start of the panary fermentation in fresh or frozen lumps of dough is delayed for several hours, exploiting the progressive softening of the coating substance used. Such particles do not therefore make it possible to ensure mechanical protection against compression, nor efficient thermal protection.

The patent WO 9212234 relates to bacteria encapsulated in fatty acids, and more particularly to *Enterococcus faceium* encapsulated in stearic acid. The capsules are formed from a paste made up of bacteria and fatty acids closely mixed together, and are presented as microspheres of binding material in which the bacteria are dispersed in a random manner. Such capsules do not include a protective layer deposited regularly on the microorganism providing chemical stability and homogenous mechanical and thermal resistance. The method of manufacture mixing the molten binding material and the bacteria limits this technique to the coating of rare microorganisms surviving treatment at high temperatures, the melting temperature of stearic acid being 70±1° C. Moreover, the size of the microspheres obtained is between 75 and 300 µm, which further limits the application of the method to the coating of initial cell clusters which are of a size smaller than these values (and poses furthermore problems of clogging during handling).

The patent U.S. Pat. No. 4,888,171 describes a granular product made up of a core, formed from crystallised sugar for example, the latter being coated with a composition adhering to it, formed from the mixture of a binding material, with a melting point of between 25 and 60° C., and dried bacterial cells. The product obtained has a stratified structure surrounding the core. This product is prepared by a method according to which the binding material is vaporised in a granulation chamber in a manner concomitant with the feeding of dried bacterial cells, the ambient temperature of the chamber being between 25 and 55° C. Thus for a coating material which has a melting point greater than 60° C., the granulation chamber will have to be kept at a temperature greater than 55° C., at which the microorganisms are partially killed or are so damaged that they then perish. This is the reason why this method is restricted to the use of coating materials, the melting point of which is lower than 60° C.

All the techniques previously described involve disadvantages connected with the necessity of reconciling aggressive manufacturing methods and fragile biological entities, which constitutes an obstacle to obtaining efficient and durable protection of living microorganisms, which has not been overcome up to present.

Thus the technical solutions proposed do not permit simultaneously:
  preparing protective particles of living microorganisms,
  and preserving the microorganisms during the manufacture of said particles.

Indeed up to present, either the coating material has quite a low melting point so as not to damage the microorganisms during the preparation of the particles, but it is not solid at ambient temperature and such particles cannot ensure efficient and durable protection; or raised temperature conditions are applied to obtain the melting of the material which has to cover the cells, making it possible to obtain solid particles which are resistant to ambient temperature, but which seriously damage the viability of the microorganisms.

It appears therefore that up to present, it has not been possible to produce, from clusters of cells of pre-existing dehydrated living microorganisms, coated particles which present a high resistance to physico-chemical stresses such as heat, humidity, gastric acidity or pressure in an efficient and durable manner, and which can be used in the applications of dietetics, pharmacology and the food-processing industry.

The particles according to the invention have the advantage of good resistance to mechanical stress, excellent chemical stability in hardly restrictive storage conditions and for the use sought, allied with a perfect viability thanks to the perfecting of a simple process of general importance making it henceforth possible to use a large number of substances for the coating and protection of the most varied living microorganisms.

The principle of the preparation method used in the present invention rests on the rapid cooling of micro-drops of the coating substance when they are injected into a granulation chamber, the chamber containing the microorganisms to be coated being kept at a regulated temperature compatible with the survival of the microorganisms. The choice of the coating substance is therefore no longer dependent on the compatibility between its melting point and the temperature tolerated by the microorganism during preparation but solely on desired criteria for the final product.

It is possible, for example, to use a coating material, the melting point of which is greater than the temperature of the human body, such that the particles do not melt and remain inactive when ingested so as to release the useful microorganism or microorganisms only once they are in the stomach. If, furthermore, the selected coating material is capable of resisting, at least partially, the attack of the gastric juices, it will be possible to provide the useful flora beyond the gastric barrier.

The properties of high mechanical resistance are obtained by the combination of two factors essentially. On the one hand, the coating substance is chosen to be in a solid state at the preservation temperature, and on the other hand, the particles are formed from a single layer of hydrophobic material, covering in a homogenous fashion the cluster of dried cells, not having any cavities showing on the surface so as not to facilitate the formation of fissures and chemical attacks, nor breaking and crushing.

Finally, the particles which are the object of the present invention are particularly easy to use because they have a granulometry which provides them with quite considerable flow properties during the preparation and handling of the particles, the latter maintaining a fluidity comparable to that of a liquid and not causing any clogging.

Thus the present invention, by a judicious choice of different chemical and physical parameters which will be explained hereinafter, proposes particles provided with original properties containing living microorganisms of a varied nature, and a method of producing said particles making it possible to reconcile the various technical exigencies during their manufacture, preservation and use.

The solution to the problem posed resides in the realisation of particles made up of a cluster of dehydrated living microorganisms and a layer of homogenous hydrophobic coating.

The hydrophobic layer is composed principally of a substance selected from fats, and in particular from fatty acids or waxes, either pure or mixed together. The essential characteristic of the coating layer is its melting point which can be between 20 and 100° C., preferably between 30 and 80° C. Saturated fatty acids are preferred and in particular stearic acid. Palmitic acid can also be used for its technical qualities. Animal or vegetable waxes such as Carnauba wax are equally suitable.

To this coating layer it is possible to add other additive molecules, such as antioxidants, sugars or proteins, known to improve the stability of microorganisms in the conditions of manufacturing and/or preserving microorganisms coated according to the invention.

The coating layer covers the cell clusters in a homogenous manner, i.e. its thickness varies very little and above all it has a uniform structure and does not contain inclusions or cavities which could affect the regularity of its surface, and consequently its rigidity and its cohesion. It is also chemically homogenous.

The choice of compounds compatible with the expected uses of the particles according to the invention is of course recommended. In particular one will chose by preference materials which meet the criterion of food quality.

The microorganisms intended to be coated are living cells which have been dried by lyophilisation, atomisation or on a fluidised bed, so that they can be revived. These techniques are well known to the person skilled in the art. After crushing, cell clusters are obtained which are in the form of a more or less fine powder. These cell clusters can be substantially spherical, ovoid or elongated, smooth or rough, regular or irregular. Their size is between several microns and several millimetres.

A great variety of microorganisms, even the most fragile and the most sensitive to the conditions of the medium, are capable of entering into the preparation of particles according to the invention, insofar as the method of manufacturing the particles is not at all aggressive in comparison with techniques known previously. Let us quote the bacteria for food, dietary or pharmaceutical use such as for example the lactobacilli, especially *Lactobacillus casei, L. casei rhamnosus, L. acidophilus, L. bulgaricus, L. brevis, L. helveticus*, the bifidobacteria; streptococci, especially *Streptococcus thermophilus, Streptococcus salivarius*; Lactococci such as *Lactococcus lactis*; the Pediococci especially *Pediococcus acidilactici*; the enterococci; the yeasts of the genus Saccharomyces (in particular *Saccharomyces cerevisiae, S. boulardii*), *Kluyveromyces*, etc. The choice of one or a mixture of these organisms will be determined above all by the final application for which it is intended, the relatively gentle manufacturing conditions proposed by the present invention not constituting the limiting criterion.

The dry powders of the above-mentioned microorganisms, obtained by lyophilisation, by atomisation or by drying in a fluidised bed, are suitable as the starting material, this list not being restrictive. Thus, the particles according to the invention can also contain microorganisms belonging to other species and being of interest for other fields of application, such as cosmetics, the protection of the environment, industrial processes requiring for example the regulated supply of additives, or any other field.

In the particles according to the invention, the proportion of coating material in relation to the quantity of microorganisms is between 10 and 99% by weight, advantageously between 30 and 80%. If the coating layer is too fine, the protection will not be sufficient; conversely, if the layer is too thick, the release of the microorganisms will be longer. This parameter will thus be adjusted according to the intended final application, depending on the desired speed of release of the microorganisms.

The concentration of viable bacteria in the coated particles is induced from the relative proportion of the coating substance and the dried powder used. Indeed, the number of microorganisms per gram of dried powder being known before coating, it is possible to calculate the concentration per particle after coating. This theoretical value is compared with the actual value measured by standard methods, as a control.

The concentration of viable bacteria is expressed as UFC/g: unit forming colony per gram of coated particles of the relevant microorganism. The measuring method is based on microbiological counting on a Petri dish, after appropriate dilution, according to the techniques known to the person skilled in the art.

The final particles have a controlled size, depending on the size of the clusters of microorganisms of the starting powder and on the thickness of the deposited coating, with an average diameter which can vary between 100 and 5000 μm, preferably between 300 and 2000 μm. It is possible to vary the size of the freeze-dried clusters depending on the intended application, using any technique at the disposition of the expert, for example by prolonged grinding.

The present invention relates also to a method of producing particles of coated microorganisms such as described previously, consisting in injecting into a chamber molten hydrophobic material, in a mass of microorganisms permanently crushed by rotation of the disc which acts as the base of the chamber, and swept by a current of dry air at a fixed temperature.

It has in fact been found in a surprising manner that it was possible to obtain, by injecting molten hydrophobic products into a chamber where the particles were subjected to rotary agitation and to sweeping by an airflow, the parameters being judiciously selected, coated particles which have the desired characteristics of physical and chemical stability.

The coating method uses a standard commercial apparatus, called a granulator, available in different sizes compatible with production volumes from several hundreds of grams to several hundreds of kilograms per operation.

FIG. 1 gives a schematic representation of the device. Referring to this drawing, the device comprises a stainless steel chamber, the base (2) of which is made up of a disc which is animated with a rotary movement by a motor (3). An airflow is injected via the space (4) between the base (2) and the body (1) of the chamber. The air escapes from the chamber via a filter (5) placed in the upper portion of the chamber. The mass of powdered microorganisms (6) is agitated by the rotation of the disc (2). A nozzle (7) permits the injection, by means of a pump (8), of the coating product kept at a temperature above its melting point in a temperature-controlled receptacle (9).

In the implementation of the method according to the invention, the parameters of which the choice is critical for obtaining a homogenous coating are the temperature of the coating product, the temperature of the air sweeping the chamber, the speed of rotation, the rate of injection of the coating, and the mass of products used. Examples 1 to 4 illustrate particular embodiments of the invention without limiting the scope however.

The temperature of the coating substance placed in the temperature-controlled receptacle (9) can be between 30 and 120° C., preferably between 60 and 120° C. In any case, it ought to be greater than the melting point of said substance, whether this is a pure product or a mixture.

The temperature of the air sweeping the granulation chamber is between 10 and 50° C. It is strictly controlled, so that at the moment of injecting the molten coating, the rise in temperature experienced by the microorganisms does not exceed a few degrees, at maximum 5° C. For certain microorganisms which cannot tolerate temperatures greater than 40° C. the temperature of the chamber will obviously be reduced.

The speed of rotation and the rate of injecting the coating are interdependent parameters and connected to the masses of the products used. The speed of rotation is generally between 50 and 500 rpm (rotation per minute). The injection of the coating can be carried out with the aid of one or more nozzles distributed over the periphery of the chamber.

All the parameters are also adjusted as a function of the shape of the initial cell clusters, and of the nature of the coating product.

The advantages of the method such as described above lie in the possibility of coating in a non-aggressive manner microorganism cells of varied shape and size, with a resistant hydrophobic layer permitting efficient and durable protection, as well as in the numerous possibilities of application offered by such properties because of the great diversity of the organisms which can be coated in this way, especially in the pharmaceutical, dietary or food fields.

The object of the invention is also the use of the previously described particles in the pharmaceutical, dietary or food-processing fields. In particular the invention permits the addition of microorganisms to different food products such as cereals, confectionery, powdered milk, in tablets etc. . . . whilst permitting a sufficient viability of said microorganisms during the manufacture of said products and for the duration of the storage preceding consumption. It also makes it possible to protect the microorganisms against gastric acidity for better activity in the intestine. Because of the original properties of the particles according to the invention, numerous other uses can also be envisaged.

The following examples illustrate in a non-restrictive manner, embodiments of the present invention and the parameters used for the production of different types of particles.

EXAMPLE 1

Coating of *Lactobacillus acidophilus* with Stearic Acid 600 g of a freeze-dried powder of bacteria *Lactobacillus acidophilus*, strain R052, registered at the CNCM under no. 1-1722, marketed by the Institut Rosell, 8480 boulevard Saint Laurent, Montreal, Canada are introduced into a granulator with a flow of air, brand name Glatt, model GPCG1, in a "rotor" configuration with a capacity of 3 litres. 900 g of stearic acid (Fluka, reference 85683, melting point mp=69–71° C.) are introduced into the temperature-controlled receptacle (9).

The coating operation is conducted according to the following parameters:
  rotor speed: 300 rpm
  speed of the air in the chamber: 3 to 4 m/s or 40% opening of the entry flap
  pulverisation pressure of the coating material: 2 bars
  coating rate: 40 g/minute
  temperature of the pulverisation air: 120° C.
  temperature of the stearic acid: 100° C.
  temperature of the incoming air: 30° C.
  temperature of the product: 32–35° C.

At the end of the operation, the granulator is empty and the particles are collected and stored in airtight sachets.

The particles thus obtained have the following characteristics:
The average diameter of the particles is 400 µm, with 92% between 100 and 600 µm.
The content of coating material is 60%.
The concentration of viable bacteria of the starting powder is $3,2.10^{11}$ UFC/g (units forming colonies per gram), that of the coated particles is $1,2.10^{11}$ UFC/g of powder introduced initially.

EXAMPLE 2

Coating of *Lactobacillus casei* by a Mixture of Fatty Acids 600 g of a freeze-dried powder of *Lactobacillus casei*, strain EQ 85 (registered at the CNCM under the number MA 64U), marketed by Lallemand SA, 15130 Saint Simon (in Canada?), are introduced into the same granulator as the one used in example 1 and the coating is placed in the temperature-controlled receptacle. The coating product is a mixture of stearic acid and palmitic acid in equal parts, the melting point of which is mp=55° C., marketed by Exaflor (47, allée de Chanteraine, 91190 Gif sur Yvette, France), under the designation Stéarine™ 50/50.

The parameters used are the same as those mentioned in example 1, with the exception of:
  the temperature of the coating: 80° C.
  the temperature of the incoming air: 25° C.
  the temperature of the product: 28–32° C.

The particles obtained have the following characteristics:
They have an average diameter of 750 µm with 90% between 100 and 1000 µm.

The content of fatty acid is 60%.
The concentration of viable bacteria of the initial powder is $4,8.10^{11}$ UFC/g, that of the coated particles is $1,6.10^{11}$ UFC/g.

EXAMPLE 3

Coating of Saccharomyces cerevisiae by a Vegetable Wax 750 g of a preparation of dry yeast Saccharomyces cerevisiae, strain deposited at the CNCM under the number I 1079, marketed under the brand name Levucell SB, by Lallemand Sarl 15130 Saint Simon, Canada are introduced into the granulator with an airflow used in example 1, and coated with 750 g of a vegetable wax, Carnauba wax, the melting point of which is mp=83–88° C. (marketed by Exaflor, Gif sur Yvette, France).

The parameters are identical to those of example 1, apart from:
the temperature of the wax: 120° C.
the temperature of the incoming air: 40° C.
the temperature of the product: 45–48° C.

The particles obtained have the following characteristics:
They have an average diameter of 1200 μm, with 90% between 500 and 2500 μm.
The content of fatty acid is 50%.
The concentration of viable cells of the initial powder is $3.10^{10}$ UFC/g, that of the coated particles is $1,45.10^{10}$ UFC/g of the starting powder.

EXAMPLE 4

Coating of Pediococcus acidilactici in a Mixture of Fatty Acids 80 kg freeze-dried powder of Pediococcus acidilactici, strain filed the CNCM under the number MA 18/5M, marketed by Lallemand SA, 15130, Saint Simon, Canada under the brand name Bactocell, are introduced into a GLATT™ granulator, model CRG200, with a capacity of 450 litres, equipped with two injection nozzles. The freeze-dried cells are coated with 160 kg of Stéarine 50/50(TM) (Exaflor, Gif sur Yvette, France).

The parameters for preparing particles are:
speed of the rotor: 120 rpm
air flow: 1500 to 2000 m³/h
pulverisation pressure: 5 bars
flow of the fatty acid: 800 g/mn (400 g/mn per nozzle, on two nozzles)
temperature of the coating material: 80° C.
temperature of the pulverisation air: 120° C.
temperature of the incoming air: 25° C.
temperature of the product at 30° C.±2° C.

The particles obtained have the following characteristics:
The average diameter is 400 μm, with 87% between 100 and 600 μm.
The content of coating material is 75%.
The concentration of viable bacteria of the initial powder is $3.10^{11}$ UFC/g, that of the coated particles $7,5.10^{10}$ UFC/g.

EXAMPLE 5

Thermal Stability

The viability of the bacteria Lactobacillus acidophilus in the freeze-dried powder used in example 1 on the one hand, and in the coated particles obtained according to this same example 1 on the other hand, have been studied in the following conditions:

Samples of 10 grams of each preparation are introduced into sealed tubes, kept in a water bath at 50° C. A tube of each preparation is withdrawn from the water bath after 1 hour, 4 hours, 7 hours and 24 hours and the concentration of viable bacteria is immediately determined.

The results are listed in table 1 below. The concentrations are expressed in UFC/g and in a percentage of the concentration of each sample at T=0:

TABLE 1

| Time | 0 | 1 month | 2 months | 3 months | 4 months |
|---|---|---|---|---|---|
| Freeze-dried powder | $3,1.10^9$ (100%) | $1,3.10^9$ (42%) | $1,2.10^9$ (38%) | $9,9.10^8$ (32%) | $4,8.10^8$ (15%) |
| Coated particles | $7,5.10^8$ (100%) | $6,4.10^8$ (85%) | $5,5.10^8$ (73%) | $5,3.10^8$ (71%) | $5,2.10^8$ (69%) |

The stability at 50° C. of the bacteria in the form of particles coated according to the present invention is clearly improved by comparison with that of the bacteria in the form of freeze-dried powder.

EXAMPLE 6

Stability in Powdered Milk

The viability of the bacteria Pediococcus acidilactici in the freeze-dried powder used in example 4 on the one hand, and in the coated powders obtained according to this same example 4 on the other hand, has been studied in the following conditions:

The preparations of bacteria are mixed into powdered milk (brand name Régiliat) at a rate of 1% by weight of bacterial preparation for 99% of milk powder. The mixtures are divided into samples of 100 grams in welded polythene sachets. The sachets are kept at 30° C. in an incubator. Each month, a sachet of each mixture is analysed for its content of viable bacterial.

The results are listed in table 2 below, the concentrations are expressed in UFC/g and in a percentage of the concentration of each sample at T=0.

TABLE 2

| Time | 0 | 1 h | 4 h | 7 h | 24 h |
|---|---|---|---|---|---|
| Freeze-dried powder | $3,1.10^{11}$ (100%) | $2,9.10^{11}$ (93%) | $1,1.10^{11}$ (35%) | $9.10^{10}$ (29%) | $2,5.10^9$ (8%) |
| Coated particles | $1,2.10^{11}$ (100%) | $1,2.10^{11}$ (100%) | $1,2.10^{11}$ (100%) | $1,1.10^{11}$ (92%) | $9.10^{10}$ (69%) |

In the presence of powdered milk at 30° C., the stability of the bacteria in the form of particles coated according to the present invention is clearly improved by comparison with that of the bacteria in the form of freeze-dried powder.

EXAMPLE 7

Gastric Stability

The stability of the bacteria Lactobacillus acidophilus in conditions simulating passing into the stomach have been studied according to the following protocol:

Two samples are prepared, one from the freeze-dried powder such as used in example 1 and the other from particles coated according to this same example 1. For each sample, 1 gram of freeze-dried powder or of coated particles is introduced into a flask containing 100 ml of a hydrochloric acid solution 0.1N (pH 1.2). The flask is placed under agitation in a water bath at 37° C. for one hour. The suspension is then centrifuged, and the remainder is taken up into 100 ml of phosphate buffer with a pH of 7.0. The residual concentration of viable bacteria is then determined and compared with that of a control in which the hydrochloric acid is replaced by a buffered solution with a pH of 7.0.

In these conditions, the *Lactobacillus acidophilus* bacteria in the form of freeze-dried powder are practically entirely destroyed (survival rate less than 0.01%) whilst the same bacteria contained in the coated particles have a survival rate of 15%.

The stability of the bacteria *Lactobacillus casei* has been studied according to the same protocol. The *Lactobacillus casei* bacteria contained in the freeze-dried powder such as used in example 2 are practically entirely destroyed by the gastric test (survival rate less than 0.01%) whilst the same bacteria contained in the particles coated according to this same example 2 have a survival rate in this same test of 25%.

EXAMPLE 8

Stability Against Compression

Tablets based on the microorganisms *Lactobacillus acidophilus, Lactobacillus casei, Saccharomyces cerevisiae* and *Pediococcus acidilactici*, dried by lyophilisation, such as described in examples 1, 2, 3 and 4 respectively, are prepared according to the following protocol:

For each microbial sample, the freeze-dried powder is mixed at a rate of 5% by weight into an excipient composed in the following manner:
49% sorbitol, (reference Neosorb 60w UPSA),
49% lactose, (Fast flow Seppic)
2% magnesium stearate (UPSA)

Each mixture is introduced successively into a tabletting apparatus of an alternating type, model EKOD marketed by Korsch. The compression forces exerted are 17500 N on the upper piston and 16400 N on the lower piston.

The concentrations of viable cells are determined in each mixture before compression, then in the tablets. The results, expressed as a percentage of survival after compression, are listed in the following table 3:

TABLE 3

| Species | Lactobacillus acidophilus | Lactobacillus casei | Saccharomyces cerevisiae | Pediococcus acidilactici |
| --- | --- | --- | --- | --- |
| Non-coated powder | 44% | 3% | 2% | 48% |
| Coated particles | 98% | 10% | 16% | 100% |

Survival after compression of the bacteria or yeasts contained in the coated particles is clearly improved by comparison with the corresponding non-coated powders.

The invention claimed is:

1. A method of coating dehydrated living microorganisms characterised in that a molten hydrophobic substance having a melting point higher than 60° C. is injected at a temperature of at least 5° C. higher than the melting temperature of said hydrophobic substance, said injection temperature being between 65° C. and 120° C., into a chamber containing said microorganisms which are agitated by rotation of the base of said chamber and swept by a flow of air at a temperature of between 10° C. and 50° C., said airflow having a sweeping speed so that the temperature in the chamber does not exceed by more than 5° C. the viability temperature of said microorganisms, and wherein particles made of a cluster of dehydrated living microorganisms and a homogenous hydrophobic coating layer are obtained.

2. The method of coating dehydrated living microorganisms according to claim 1, characterised in that the speed of rotation of the base of said chamber is between 50 and 500 rpm.

3. The method of coating dehydrated living microorganisms according to claim 1, characterised in that said hydrophobic coating substance has a melting point of between 60° C. and 100° C.

4. The coating method according to claim 1, characterised in that said hydrophobic coating substance is selected from the group consisting of fats, fatty acids, waxes, and mixtures thereof.

5. The coating method according to claim 1, characterised in that said dehydrated living microorganisms are selected from the group consisting of lactobacilli, bifidobacteria, streptococci, streptococci faecalis, pediococci, yeasts, and a mixture thereof.

6. The coating method according to claim 1, characterised in that the proportion of said injected coating substance is between 10 and 99%, by weight of the final particles.

7. The method according to claim 1, wherein the chamber temperature is between approximately 30 and 55° C.

8. The method according to claim 4, wherein the melting point is between 60° C. and 80° C.

9. The method according to claim 6, wherein the proportion of said injected coated substance is between 30 and 80%.

10. A method of coating dehydrated living microorganisms, comprising:

introducing said microorganisms into a chamber having a base;

agitating said microorganisms by rotation of the base of said chamber;

providing a flow of air at a temperature of between 10° C. and 50° C., said airflow having a sweeping speed so that the temperature in the chamber does not reach a temperature of more than 5° C. of the viability temperature of said microorganisms; and thereafter injecting a molten hydrophobic substance having a melting point higher than 60° C. into said chamber containing said microorganisms at a temperature of at least 5° C. higher than the melting temperature of said hydrophobic substance, said injection temperature being between 65° C. and 120° C., and wherein particles comprising dehydrated living microorganisms having a homogenous hydrophobic coating layer covering said microorganisms are obtained.

11. The method of coating dehydrated living microorganisms according to claim 10, wherein the speed of rotation of the base of said chamber is between 50 and 500 rpm.

12. The method of coating dehydrated living microorganisms according to claim 10, wherein said hydrophobic coating substance has a melting point of between 60° C. and 100° C.

13. The coating method according to claim 10, wherein said hydrophobic coating substance is selected from the group consisting of fats, fatty acids, waxes, and mixtures thereof.

14. The coating method according to claim 10, wherein said dehydrated living microorganisms are selected from the group consisting of lactobacilli, bifidobacteria, streptococci, streptococci faecalis, pediococci, yeasts, and a mixture thereof.

15. The coating method according to claim 10, wherein the proportion of said injected coating substance is between 10 and 99%, by weight of the final particles.

16. The method according to claim 10, wherein the chamber temperature is between approximately 30 and 55° C.

17. The method according to claim 13, wherein the melting point is between 60° C. and 80° C.

18. A method of coating dehydrated living microorganisms, comprising:
introducing a cluster of cells comprising said microorganisms into a chamber having a base;
agitating said cluster of cells comprising said microorganisms by rotation of the base of said chamber;
providing a flow of air at a temperature of between 10 and 50° C. into said chamber, said airflow having a sweeping speed so that the temperature in the chamber does not exceed by more than 5° C. of the viability temperature of said microorganisms; and thereafter
providing a molten hydrophobic substance having a melting point higher than 60° C. into said chamber containing said cluster of cells comprising said microorganisms at a temperature of at least 5° C. higher than the melting temperature of said hydrophobic substance to obtain particles comprising said cluster of cells comprising said microorganisms and a homogenous hydrophobic coating layer.

19. The method according to claim 18, wherein the melting point is between 60° C. and 100° C.

20. The method according to claim 18, wherein the melting point is between 69° C. and 100° C. and the injection temperature is between 74° C. and 120° C.

* * * * *